(12) United States Patent
Benz et al.

(10) Patent No.: US 10,495,881 B2
(45) Date of Patent: Dec. 3, 2019

(54) EYEGLASSES HAVING AT LEAST ONE PARTIALLY TRANSPARENT SCREEN, AND METHOD FOR OPERATION OF EYEGLASSES

(71) Applicant: bredent medical GmbH & Co. KG, Senden (DE)

(72) Inventors: Roland Benz, Ulm (DE); Gerald Micko, Laupheim (DE)

(73) Assignee: bredent medical GmbH & Co. KG, Senden (DE)

( * ) Notice: Subject to any disclaimer, the term of this patent is extended or adjusted under 35 U.S.C. 154(b) by 0 days.

(21) Appl. No.: 15/954,724

(22) Filed: Apr. 17, 2018

(65) Prior Publication Data

US 2018/0299675 A1 Oct. 18, 2018

(30) Foreign Application Priority Data

Apr. 18, 2017 (DE) ........................ 10 2017 108 235

(51) Int. Cl.
*G02B 27/01* (2006.01)
*H04N 13/189* (2018.01)
(Continued)

(52) U.S. Cl.
CPC .......... *G02B 27/0172* (2013.01); *A61B 34/25* (2016.02); *A61B 90/361* (2016.02);
(Continued)

(58) Field of Classification Search
CPC ............ G02B 27/0172; G02B 27/0179; G02B 2027/0141; G02B 2027/0178; G02B 2027/0138; H04N 13/239; H04N 13/344; H04N 13/189; H04N 2213/001; H04N 2213/008; A61B 90/361; A61B 90/37; A61B 34/25; A61B 1/00009; A61B 1/24;
(Continued)

(56) References Cited

U.S. PATENT DOCUMENTS 9,936,166 B2    4/2018  Lindenberg et al.
2014/0154655 A1* 6/2014  Bell .................. G09B 23/28
                                           434/262

(Continued)

FOREIGN PATENT DOCUMENTS

DE  10 2012 221 374 A1    5/2014
WO     2015/143508 A1    10/2015

OTHER PUBLICATIONS

Wang et al., "Augmented Reality Navigation With Automatic Marker-Free Image Registration Using 3-D Image Overlay for Dental Surgery," IEEE Transactions on Biomedical Engineering, vol. 61, No. 4, Apr. 2014, pp. 1295-1304.

*Primary Examiner* — Marnie A Matt
(74) *Attorney, Agent, or Firm* — Collard & Roe, P.C.

(57) ABSTRACT

Eyeglasses have at least one partially transparent screen as an eyeglass lens and multiple optical recording apparatuses for recording images in a field of vision of a user of the eyeglasses. The recorded images can be processed further by a processing apparatus, in such a manner that a position of the eyeglasses relative to a patient can be determined, and, based on this position, a position of a planned implant in the jaw of a patient can be represented on the at least one partially transparent screen in the form of a marking.

13 Claims, 3 Drawing Sheets

(51) Int. Cl.
- A61B 34/00 (2016.01)
- A61C 8/00 (2006.01)
- G02C 11/00 (2006.01)
- A61B 90/00 (2016.01)
- *A61B 1/24* (2006.01)
- *A61B 90/50* (2016.01)

(52) U.S. Cl.
CPC ............ *A61B 90/37* (2016.02); *A61C 8/0089* (2013.01); *G02B 27/0179* (2013.01); *G02C 11/10* (2013.01); *H04N 13/189* (2018.05); *A61B 1/24* (2013.01); *A61B 2034/252* (2016.02); *A61B 2090/365* (2016.02); *A61B 2090/371* (2016.02); *A61B 2090/372* (2016.02); *A61B 2090/373* (2016.02); *A61B 2090/502* (2016.02); *G02B 2027/0138* (2013.01); *G02B 2027/0141* (2013.01); *G02B 2027/0178* (2013.01); *H04N 2213/001* (2013.01); *H04N 2213/008* (2013.01)

(58) Field of Classification Search
CPC ........ A61B 2090/371; A61B 2090/365; A61B 2090/502; A61B 2090/372; A61B 2090/373; A61B 2034/252; A61C 8/0089; A61C 2204/005; G02C 11/10
USPC .......................................................... 348/66
See application file for complete search history.

(56) References Cited

U.S. PATENT DOCUMENTS

| | | | |
|---|---|---|---|
| 2015/0296184 A1* | 10/2015 | Lindenberg | A61C 9/0046 348/77 |
| 2016/0358327 A1* | 12/2016 | Lemchen | G06T 7/248 |
| 2017/0105802 A1* | 4/2017 | Taraschi | A61B 50/26 |
| 2018/0168780 A1* | 6/2018 | Kopelman | A61C 1/0015 |
| 2018/0322702 A1* | 11/2018 | Djajadiningrat | A61N 1/3993 |
| 2018/0344408 A1* | 12/2018 | Rotilio | G02B 27/017 |

\* cited by examiner

EYEGLASSES HAVING AT LEAST ONE PARTIALLY TRANSPARENT SCREEN, AND METHOD FOR OPERATION OF EYEGLASSES

CROSS REFERENCE TO RELATED APPLICATIONS

Applicant claims priority under 35 U.S.C. § 119 of German Application No. 10 2017 108 235.2 filed Apr. 18, 2017, the disclosure of which is incorporated by reference.

BACKGROUND OF THE INVENTION

1. Field of the Invention

The invention relates to eyeglasses having at least one partially transparent screen, and to a method for operation of eyeglasses.

2. Description of the Related Art

For dental prosthetic care of patients, it is usual, among other things, to place one or more implants into the jawbone in place of one or more teeth. To place the implants, two-dimensional and three-dimensional X-rays are taken, which represent the Anatomical Situation for the treating dentist. In this way, the dentist can select and place the implants. In addition to the X-rays, scan data are also compiled.

The scan data describe the position of the abutment in the environment of adjacent teeth. For complete recording of the geometry, records are created in multiple scan passes, with different viewing angles and recording regions, and combined to provide an overall image representation. This three-dimensional planning for modeling of a prosthesis as well as for positioning of implants can be undertaken using a commercially available planning program. In these planning programs, the X-ray data and scan data are combined.

From the general state of the art, it is known to use corresponding templates for placement of implants within the scope of guided implantation, which templates support placement of an implant. Likewise, however, placement of an implant is often carried out without aids, merely on the basis of the skill of a dentist or a surgeon. In the latter case, in particular, an improved monitoring possibility of the work of the dentist or of the surgeon would already be desirable during the operation.

Furthermore, it is known that aside from the scanning procedures and three-dimensional planning programs already mentioned, other modern technologies of digital image processing are also increasingly being used in the field of dentistry.

Thus, an apparatus is known from the article by Wang et al., "Augmented Reality Navigation With Automatic Marker-Free Image Registration Using 3-D Image Overlay for Dental Surgery," IEEE Transactions on Biomedical Engineering, Vol. 61, No. 4, April 2014, page 1296-1304, in which image data such as MRT or X-ray images as well as planned implant insertions are projected onto the patient by way of a semipermeable mirror. In this way, the operating surgeon can introduce the implants in the previously calculated position, following these data.

The document DE 10 2012 221 374 A1 shows a method for planning and monitoring of a dental treatment, among other things. In this method, patient data are recorded by means of a camera, and subsequently image data such as X-ray images are superimposed on them. The combination of the actual data and the examination results are available to the treating dentist by means of a display. Aside from representation of the image data on a monitor, representation by means of virtual monitor eyeglasses or another Virtual Reality display apparatus is also proposed.

The document WO 2015/143508 A1 shows a method for planning of implantological operations as well as for navigation during the operations. For this purpose, the operation tools used by the treating dentist are provided with marking devices, which can be detected by a camera. In this regard, the position of the tools and, connected with this, the subsequent position of implants, for example, can be displayed on a monitor.

Such apparatuses are therefore used during treatment, in order to guide operation tools, which makes their dissemination in dental practices very costly.

SUMMARY OF THE INVENTION

It is therefore the task of the invention to indicate eyeglasses having at least one partially transparent screen, and a method for operation of eyeglasses, which allow simple use even without any connection with operation tools, and nevertheless can bring about an improvement in dental treatment.

This task is accomplished by the eyeglasses and method according to the invention. Further advantageous embodiments of the invention are discussed below. These embodiments can be combined with one another in technologically practical manner. The description, in particular in connection with the drawing, additionally characterizes and specifies the invention.

According to the invention, eyeglasses having at least one partially transparent screen as an eyeglass lens and multiple optical recording apparatuses for recording images in a field of vision of a user of the eyeglasses is indicated, wherein the recorded images can be processed by means of a processing apparatus, in such a manner that a position of the eyeglasses relative to a patient can be determined, and, using this position, a position of a planned implant in the jaw of a patient on the at least one partially transparent screen can be represented in the form of a marking.

Accordingly, eyeglasses are created, in which a user of the eyeglasses, acting as a dentist during treatment of a patient, is supplied with additional data on the partially transparent screen, so that the data shown there with regard to the data regarding the environment is superimposed.

In order to now be able to superimpose the additional data in the form of a marking in the correct position, the relative position between eyeglasses and jaw of the patient is continuously determined, so that the additional data with regard to its coordinates comes to lie correctly within the partially transparent screen. The eyeglasses according to the invention therefore merely provide additional data, without bringing about the guidance of tools known from the state of the art. The marking is a helpful orientation for the user when setting a planned implant.

The eyeglasses themselves can, of course, include other screen regions aside from the partially transparent screen. These screen regions include, for example, set-on lenses with high magnification. Furthermore, the eyeglasses can, of course, be configured in the form of a partially transparent pane of glass with suitable attachment to the head of the user, without necessarily needing to have the elements unavoidably brought into connection with eyeglasses, such as nose bridges, side pieces or the like. The eyeglasses according to the invention therefore represent an orientation aid for the dentist during the operation for setting a planned implant.

According to one embodiment of the invention, the multiple optical recording apparatuses are formed in the form of cameras, in particular digital cameras.

In order to be able to record the environment as efficiently as possible, the use of digital cameras, for example in the form of CCD cameras, is particularly provided. These can typically be disposed in the form of a pair on opposite sides of the eyeglasses, in order to be able to carry out a three-dimensional image reconstruction.

According to a further embodiment of the invention, two partially transparent screens are provided, so that the user of the eyeglasses can recognize the marking at the position of the planned implant in three dimensions.

Accordingly, it is provided to create either two partially transparent screens or also two partially transparent screen regions, which are covered by one of the two eyes of the user, so that the usual three-dimensional ability to see is also possible with reference to the marking.

According to a further embodiment of the invention, the processing apparatus processes the images recorded by the optical recording apparatuses further, so that the determination of the position of the eyeglasses relative to the patient can be carried out using known reference points in the jaw of the patient.

In this regard the reference points can be teeth of the remainder of the set of teeth and/or implants that have already been set, with inserted auxiliary marking apparatuses, and/or auxiliary marking apparatuses attached to the teeth.

For orientation within the jaw of the patient, not only tooth positions of the remainder of the set of teeth, which were previously measured in suitable manner, or also special aids, which are set onto implants that have already been set, or onto teeth, can be used. In this way, easy determination of the position of the eyeglasses relative to the jaw of the patient is possible during use. Fundamentally, however, all components in the jaw space of the patient can be used as reference points, if they lie in the field of vision of the operator during setting of the planned implant and are fixed in place with reference to the implant position.

According to a further embodiment of the invention, the marking can be represented on the partially transparent screen(s) in the form of a line-shaped object or of a cylinder-shaped object, at the position of the planned implant.

In this regard, marking at the position of the planned implant advantageously takes place in such a manner that the marking can be clearly recognized by the user. The configuration in the form of a line or of a cylinder can be additionally facilitated by means of corresponding coloration or further designs, such as arrows or the like.

According to a further embodiment of the invention, the optical recording apparatuses and/or the partially transparent screen(s) can be transmitted, by means of one or more lines, or wirelessly by wireless transmission, to at least one control device that is coupled with the processing apparatus.

Both the data of the optical recording apparatuses and of the partially transparent screens are typically passed on to the processing apparatus by way of a control device, so that merely a local cable connection between optical recording apparatuses or partially transparent screens and the control devices is necessary. This feature significantly reduces the expenditure in designing the eyeglasses, because now not every module needs to be made available with its own connection to the processing apparatus.

According to a further embodiment of the invention, the processing apparatus is coupled with the control device by means of a wireless transmission route.

Accordingly, the connection between processing apparatus and control device advantageously takes place in cable-free manner, so that handling of the eyeglasses during an operation is possible without restrictions with regard to the freedom of movement.

Furthermore, a method for operation of eyeglasses, in particular as described above, is indicated, in which the following steps are carried out: providing eyeglasses having at least one partially transparent screen as the eyeglass lens and multiple optical recording apparatuses for recording images in a field of vision of a user of the eyeglasses, recording the starting situation in the jaw of a patient by the multiple optical recording apparatuses, establishing a position for a planned implant in the jaw of the patient, continuously associating the images recorded using the optical recording apparatuses to determine a position of the eyeglasses relative to the jaw of the patient, and outputting a marking on the partially transparent screen configured as an eyeglass lens, to identify the position for the planned implant.

In this regard, determining the position of the eyeglasses relative to the patient can be carried out using known reference points in the jaw of the patient.

In one embodiment, the screen can be configured to be partially transparent and configured as an eyeglass lens.

Accordingly, the eyeglasses can be made available as Augmented Reality eyeglasses.

As an alternative to the method described, using partially transparent eyeglasses, it is also possible to use Virtual Reality eyeglasses, in which the environmental data are supplied by way of a camera.

BRIEF DESCRIPTION OF THE DRAWINGS

Other objects and features of the invention will become apparent from the following detailed description considered in connection with the accompanying drawings. It is to be understood, however, that the drawings are designed as an illustration only and not as a definition of the limits of the invention.

In the drawings, wherein the same or functionally equivalent components are provided with the same reference symbols.

DETAILED DESCRIPTION OF PREFERRED EMBODIMENTS

Figure 1:
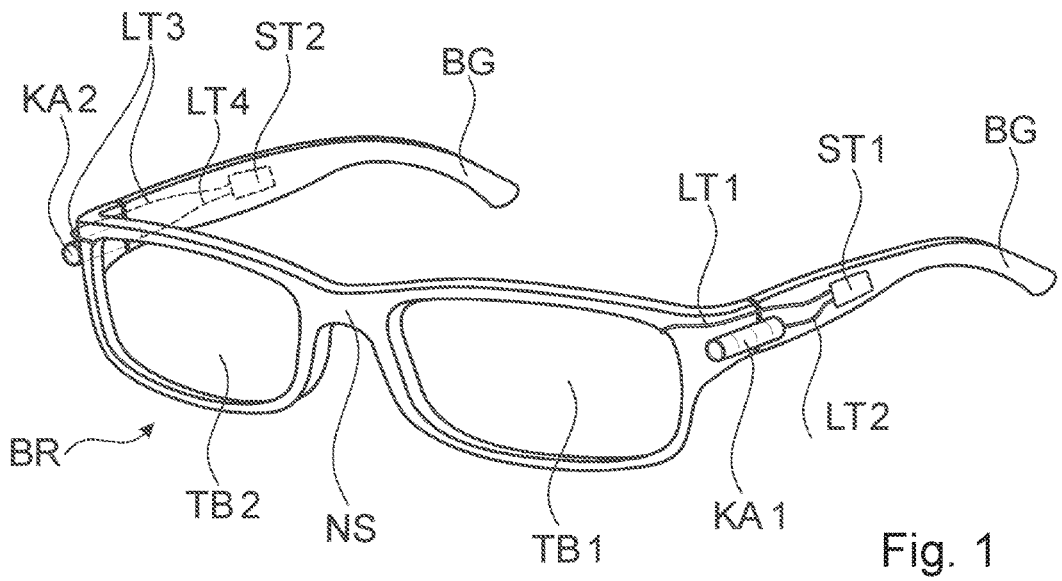
FIG. 1 shows eyeglasses according to the invention in a perspective side view.

In FIG. 1, an embodiment of eyeglasses BR according to the invention is shown in a perspective side view. In the representation according to FIG. 1, the eyeglasses BR are equipped, in accordance with a traditional vision aid, with two side pieces BG, which each make a transition into a frame for eyeglass lenses, in each instance, which are connected with one another by means of a nose bridge NS.

The form of eyeglasses BR shown in FIG. 1 should, however, be understood merely as an example, so that other embodiments, for example in the form of an individual pane of glass or light-sealed coverings passed around eyeglass lenses can be used within the scope of the invention.

In place of eyeglass lenses, a first partially transparent screen TB1 and a second partially transparent screen TB2 are fitted into the eyeglasses BR. At the transition to the side pieces BG, optical recording apparatuses in the form of a first camera KA1 and a second camera KA2 are disposed at opposite sides of the eyeglasses BR, in each instance.

The first partially transparent screen TB1 is connected with a first control device ST1 using a first line LT1. The first camera KA1 is connected with the first control device ST1 using a second line LT2. On the opposite side, the second partially transparent screen TB2 is passed to a second control device ST2 using a third line LT3. The second camera KA2 is connected with the second control device ST2 by way of a fourth line LT4.

The two control units ST1 and ST2 are structured in such a manner that not only the images in the field of vision of a user of the eyeglasses BR recorded by the optical recording apparatuses KA1 and KA2 can be transmitted, but also images that are received by way of the two control devices ST1 and ST2 can be displayed on the partially transparent screens TB1 and TB2.

Due to the partially transparent properties, the images displayed by the partially transparent screens TB1 and TB2 are superimposed on the actual field of vision of a user of the eyeglasses BR, so that in this manner, additional data can be made available.

It should be noted that the eyeglasses BR according to FIG. 1 can also be structured in such a manner, in place of the complete replacement of eyeglass lenses using the partially transparent screens TB1 and TB2, so that the partially transparent screens TB1 and TB2 are embedded into the eyeglasses BR together with other optical lenses. In yet other embodiments, it is possible to provide merely one partially transparent screen that spans both eyes of a user. The partially transparent screen(s) can, of course, also achieve three-dimensional perception by the user, at the request of the user, because different image components in the field of vision can be superimposed for each eye of the user, so that a correct three-dimensional impression is created.

The two cameras KA1 and KA2, as optical recording apparatuses, are typically disposed on opposite sides of the eyeglasses BR, in order to create a sufficiently spaced-apart triangulation base that allows three-dimensional image processing.

The eyeglasses BR shown in FIG. 1 are worn by a dentist during treatment of a patient, for example, so that during planned setting of an implant in a jaw of the patient, additional data can be represented. For this purpose, however, it is necessary to continuously determine the relative position of the eyeglasses BR with regard to the patient. For this purpose, the two cameras KA1 and KA2 are provided, which will be explained below.

Figure 2:
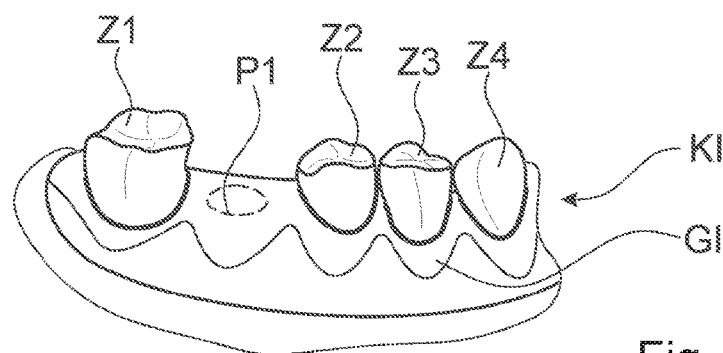
FIG. 2 is a detail of a jaw of the patient when using the eyeglasses according to the invention.

Making reference to FIG. 2, a detail of a jaw KI of a patient when using the eyeglasses BR according to the invention is shown. It can be seen that the jaw KI, in this example, comprises a remaining set of teeth, which set is formed, as an example, by the teeth Z1, Z2, Z3 and Z4. At a position P1, which is situated within a gap between the first tooth Z1 and the second tooth Z2, an implant is to be set by the treating dentist. If the position, the three-dimensional shape, and the respective transitions to gums or a gingiva GI are now known, it is possible to determine the relative position between the cameras KA1 and KA2, and therefore consequently also between the treating dentist and the jaw KI in simple manner, by recording images using the two cameras KA1 and KA2, based on these known objects. If, for example, the treating dentist changes his/her viewing direction, the optical impression of the teeth Z1 to Z4 would change accordingly, so that a change in position between eyeglasses BR and jaw KI can be determined from the deviation.

Figure 3:
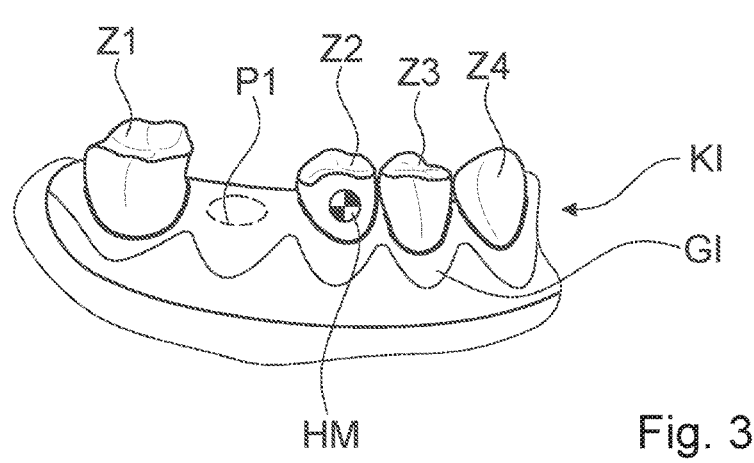
FIG. 3 is a further detail of the jaw of the patient when using the eyeglasses according to the invention.

As is shown in FIG. 3, in another embodiment the determination of the relative position between eyeglasses BR and jaw KI can also take place by means of an auxiliary marking apparatus HM, which is disposed on the first tooth Z1, as an example. It is understood that the auxiliary marking apparatus HM can also have a form different from the one shown in FIG. 3. Here, the form will be selected in such a manner that the position determination in the image processing is supported by means of the images recorded by the two cameras KA1 and KA2.

In yet another embodiment, the teeth Z1 to Z4 of the remaining set of teeth in the jaw KI are not used as reference points, but rather an auxiliary marking apparatus HM is used on an implant that has already been set.

This embodiment will be explained in greater detail making reference to FIG. 4. Here, too, an implant is to be set at the position P1, between the first tooth Z1 and the second tooth Z2. An implant IM, however, is already present between the tooth Z2 and the tooth Z4, into which the auxiliary marking apparatus HM has been inserted here in place of a crown. This auxiliary marking apparatus is shown as an object in the shape of a truncated cone in FIG. 4, as an example. It is understood that the auxiliary marking apparatus HM can assume different forms, wherein it is practical if the form is selected in such a manner that the position determination during image processing is supported by means of the images recorded by the two cameras KA1 and KA2.

Figure 4:
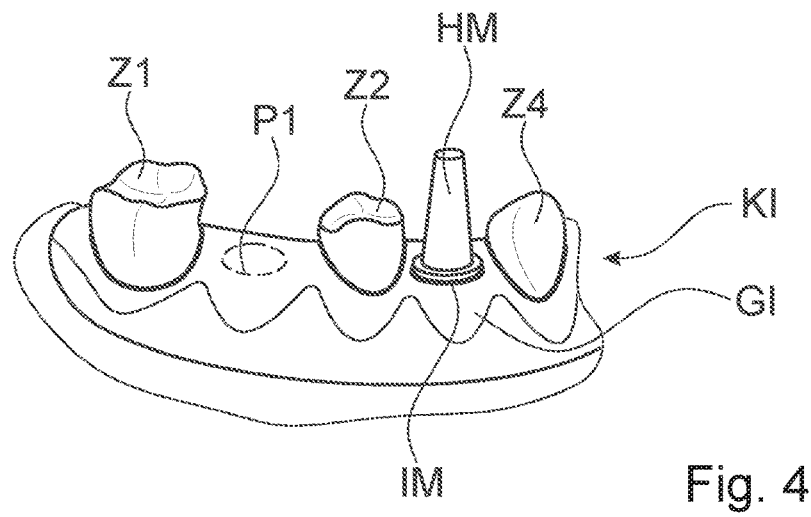
FIG. 4 is a further detail of the jaw of the patient when using the eyeglasses according to the invention.

As an end result, depending on whether the reference points used are the teeth of the remaining set of teeth according to FIG. 2, an auxiliary device on one or more teeth of the remaining set of teeth according to FIG. 3, or an auxiliary device according to FIG. 4, data are now obtained regarding the relative position between jaw KI and eyeglasses BR, so that the two partially transparent screens TB1 and TB2 can have an additional marking superimposed on them, in the correct position, in each instance, which marking makes the first position P1 in the jaw KI clear.

Figure 5:
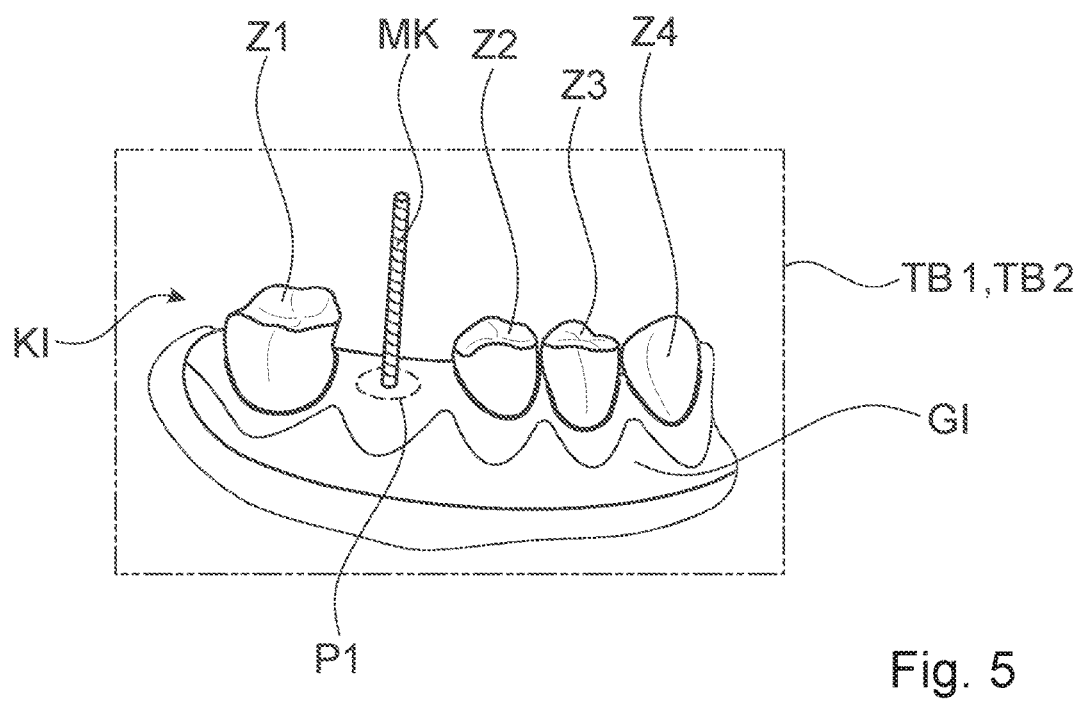
FIG. 5 shows schematically a representation on partially transparent screens as an integral part of the eyeglasses according to the invention.
Figure 6:
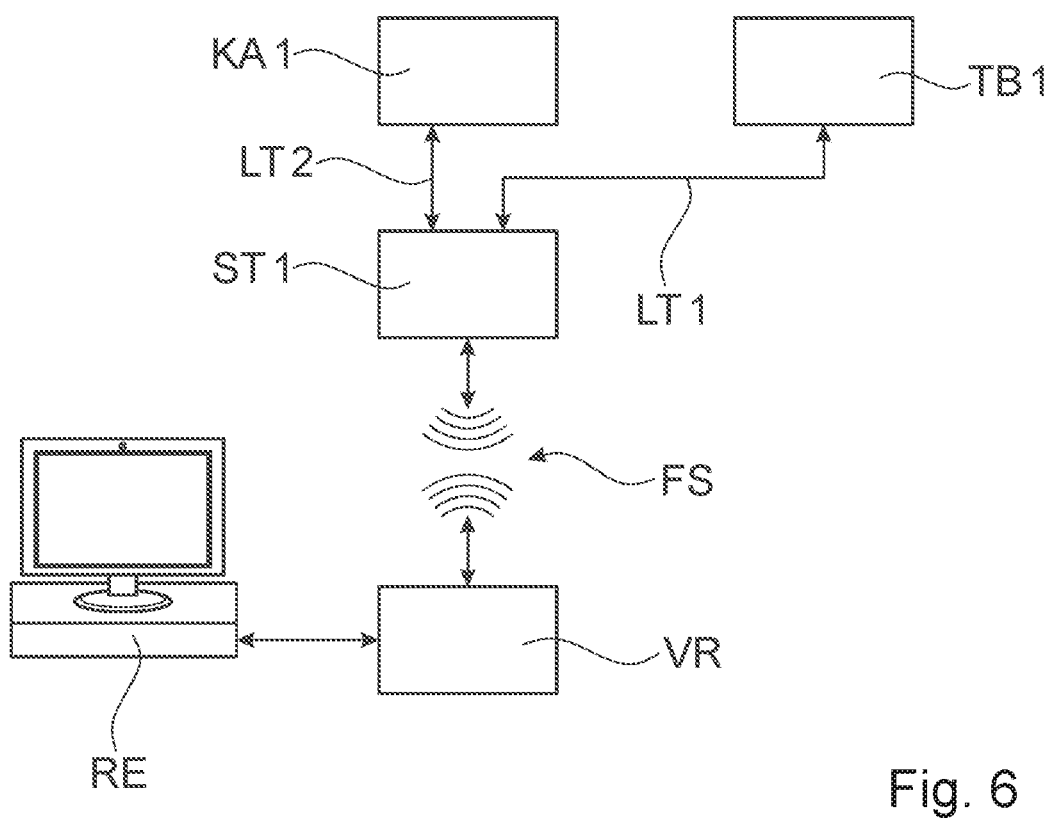
FIG. 6 shows in a block schematic, a system consisting of eyeglasses and additional operating devices.

An example of the marking is shown in FIG. 5. Here, a line-shaped or cylinder-shaped marking MK is superimposed at the position P1, in the correct position, on the two partially transparent screens TB1 and TB2, so that the user of the eyeglasses BR is given a marking at the position P1, which marking supports him/her in the planned treatment for setting of an implant. Because a marking MK is provided on both partially transparent screens TB1 and TB2, in each instance, the treating dentist can correctly perceive the marking MK in three dimensions. Use of the marking MK therefore represents a great aid in non-guided implantation, because the treating dentist is now given an indication of where the corresponding operation tools must be placed. Implantation by the dentist or surgeon therefore no longer takes place in "free hand" manner, but rather with orientation provided by the superimposed marking MK.

During use of the eyeglasses BR, the data received or transmitted by the control units ST1 and ST2 are typically passed on to a processing apparatus with a cable connection or by way of a wireless transmission route. An example of such a structure is shown as an example in FIG. 5, for the components of the eyeglasses BR assigned to the left eye. It can be seen that the first control device ST1 can exchange data with the processing apparatus VR by way of the wireless transmission route FS, wherein the processing apparatus VR in turn is connected with a computer RE. In this regard, the computer RE can ensure facilitation of the work during the planned implantation, by means of additional functions, in that recorded images of the eyeglasses BR can be reworked or analyzed offline. Likewise, the computer RE can be used for initializing or also for carrying out the aforementioned three-dimensional planning. It is understood that the processing apparatus VR can also be an integral part of the computer RE. Furthermore, the wireless transmission route FS can also be replaced by cable-connected transmission.

Provision of additional data using the marking MK was described, until now, with reference to an implant position. It is understood that the data imported into the field of vision of the treating dentist can also comprise further data, such as, for example, an axis direction of the planned implant or also the implantation depth. It is important, in this connection, that the eyeglasses according to the invention merely represent a superimposition on the real clinical situation, without intending any guidance of the operation tools. The required precision is achieved using the remaining set of teeth or other unchangeable factors such as the aforementioned auxiliary marking apparatuses, for example.

A method for operation of eyeglasses BR, after providing the eyeglasses with the screen TB1 and/or TB2 and multiple optical recording apparatuses KA1 and KA2 for recording images in a field of vision of a user of the eyeglasses, can include recording the starting situation in the jaw of a patient by means of the multiple optical recording apparatuses KA1 and KA2, determining a position P1 for a planned implant in the jaw KI of the patient and continuously associating the images recorded by means of the optical recording apparatuses KA1 and KA2 for determining a position of the eyeglasses BR relative to the jaw of the patient, outputting a marking MK on the screen TB1 and/or TB2 for identifying the position P1 for the planned implant.

If the screen TB1 and/or TB2 is/are configured to be partially transparent and configured as an eyeglass lens, AR eyeglasses (AR=augmented reality) can be used. It is also possible, however, to use VR eyeglasses (VR=virtual reality) into which data recorded by means of the optical recording apparatuses are fed.

The characteristics indicated above and in the claims, as well as the characteristics that can be derived from the figures, can advantageously be implemented individually and in different combinations. The invention is not restricted to the exemplary embodiments described, but rather can be modified in many ways, within the scope of the ability of a person skilled in the art.

Although only a few embodiments of the present invention have been shown and described, it is to be understood that many changes and modifications may be made thereunto without departing from the spirit and scope of the invention.

What is claimed is:

1. An assembly comprising:
   (a) a pair of eyeglasses; and
   (b) a processing apparatus;
   wherein the eyeglasses comprise an eyeglass lens comprising a partially transparent screen and a plurality of optical recording apparatuses for recording images in a field of vision of a user of the eyeglasses;
   wherein the images recorded are processed by the processing apparatus to determine an eyeglasses position of the eyeglasses relative to a patient and based on the eyeglasses position, a planned implant position of a planned implant in a jaw of the patient is represented as a marking on the partially transparent screen; and
   wherein the marking in the planned implant position is superimposed on an actual field of vision of a user.

2. The assembly according to claim 1, wherein the optical recording apparatuses comprise cameras.

3. The assembly according to claim 2, wherein the cameras are digital cameras.

4. The assembly according to claim 1, wherein the eyeglass lens comprises first and second partially transparent screens to permit the user of the eyeglasses to recognize the marking at the planned implant position of the planned implant in three dimensions.

5. The assembly according to claim 1, wherein the processing apparatus processes the images recorded by the optical recording apparatuses further to permit determination of the eyeglasses position of the eyeglasses relative to the patient using known reference points in the jaw of the patient.

6. The assembly according to claim 5, further comprising auxiliary marking apparatuses, wherein the reference points are at least one of teeth of a remaining set of teeth and implants that have already been set.

7. The assembly according to claim 1, wherein the marking is represented on the partially transparent screen as a line-shaped object or a cylinder-shaped object at the planned implant position of the planned implant.

8. The assembly according to claim 1, wherein the eyeglasses comprise at least one control device coupled with the processing device and at least one line, wherein data from at least one of the optical recording apparatuses and the partially transparent screen is transmitted to the at least one control device by the at least one line.

9. The assembly according to claim 8, wherein the processing apparatus is coupled with the at least one control device by a wireless transmission route.

10. A method for operation of eyeglasses comprising:
   (a) providing eyeglasses having at least one screen and a plurality of optical recording apparatuses for recording images in a field of vision of a user of the eyeglasses;
   (b) recording a starting situation in a jaw of a patient using the optical recording apparatuses;
   (c) establishing a planned implant position for a planned implant in the jaw of the patient;
   (d) continuously associating the images recorded using the optical recording apparatuses to determine an eyeglasses position of the eyeglasses relative to the jaw of the patient; and
   (e) outputting a marking on the at least one screen to identify the planned implant position for the planned implant;
   wherein the marking in the planned implant position is superimposed on an actual field of vision of the user.

11. The method according to claim 10, wherein the eyeglasses position of the eyeglasses relative to the patient is determined using known reference points in the jaw of the patient.

12. The method according to claim 10, wherein the at least one screen is partially transparent and configured as an eyeglass lens.

13. The method according to claim 10, wherein the eyeglasses comprise Virtual Reality eyeglasses and data recorded by the optical recording apparatuses are fed into the Virtual Reality eyeglasses.

* * * * *